(12) United States Patent
Asmussen et al.

(10) Patent No.: US 6,267,982 B1
(45) Date of Patent: *Jul. 31, 2001

(54) SKIN-ADHERING PHARMACEUTICAL PREPARATION, IN PARTICULAR TRANSDERMAL THERAPEUTIC SYSTEM FOR THE RELEASE OF 17-β-ESTRADIOL TO THE HUMAN ORGANISM

(75) Inventors: Bodo Asmussen, Bendorf-Sayn; Michael Horstmann, Neuwied, both of (DE)

(73) Assignee: LTS Lohman Therapie-Systeme GmbH, Neuwied (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/101,720

(22) PCT Filed: Dec. 23, 1996

(86) PCT No.: PCT/EP96/05822

§ 371 Date: Mar. 17, 1999

§ 102(e) Date: Mar. 17, 1999

(87) PCT Pub. No.: WO97/25077

PCT Pub. Date: Jul. 17, 1997

(30) Foreign Application Priority Data

Jan. 8, 1996 (DE) ............................................. 196 00 347

(51) Int. Cl.$^7$ ........................................................ A61F 13/02
(52) U.S. Cl. ............................................. 424/448; 424/449
(58) Field of Search ..................................... 424/448, 449

(56) References Cited

U.S. PATENT DOCUMENTS 4,863,738 * 9/1989 Taskovich ............................. 424/449

OTHER PUBLICATIONS

*Scrip* No. 2026, May 19, 1995 p 23.*

* cited by examiner

*Primary Examiner*—Michael A. Williamson
(74) *Attorney, Agent, or Firm*—Ann W. Speckman; James E. Klaniecki

(57) ABSTRACT

A pharmaceutical preparation adhering to the skin, in particular a TTS, for the release of the active substance 17-β-estradiol, the concentration of the estradiol contained therein in dissolved form being between its saturation concentration in equilibrium with a gas phase of less than 10% relative air humidity and its saturation concentration in equilibrium with a gas phase of more than 90% relative air humidity, in all matrix layers and, if present, also in an adhesive layer, characterized in that the estradiol quantity contained in the preparation amounts to at least three times the saturation solubility measured at 95% relative air humidity, and that the air enclosed in the package is adjusted to a relative air humidity between 5% and below 0.5%.

14 Claims, No Drawings

SKIN-ADHERING PHARMACEUTICAL PREPARATION, IN PARTICULAR TRANSDERMAL THERAPEUTIC SYSTEM FOR THE RELEASE OF 17-β-ESTRADIOL TO THE HUMAN ORGANISM

BACKGROUND OF THE INVENTION

1. Field of the Invention

The present invention relates to a pharmaceutical preparation adhering to the skin, in particular a transdermal therapeutic system, for the release of 17-β-estradiol and optionally further active substances through the skin to the human organism.

Pharmaceutical preparations contacting the skin include, for example, ointments, creams, lotions, and also drug-containing patches, these have been introduced on the market for some time under the name "transdermal therapeutic systems" (TTS) to treat several diseases.

In the meantime, TTSs comprising the active substance 17-β-estradiol have also been on the market as a therapeutic agent for climacteric complaints, and, for a short time, also against osteoporosis, proving successful in therapy.

In several cases, however, the insufficient capability of the active substance to permeate through the skin has become apparent as a disadvantage of prior art systems. This cannot be increased beyond a certain limit, the so-called "saturation flow", although numerous galenic measures with respect to the TTS-construction have been taken (use of multilayer systems, use of controlling membranes, variations of the active substance concentration, modification of the base polymer, and the like).

2. Description of the Related Art

The finding that the transdermal flow of an active substance from the solid, finely dispersed phase cannot be increased further, even if high-dissolving vehicles are used, can already be found in the trailblazing works of Higuchi (e.g., T. Higuchi: Physical Chemical Analysis of percutaneous absorption process from creams and ointments, J. Soc. Cosmetic Chem. 11, p. 85–97 (1960). However, for many active substances there is the possibility of adding so-called "enhancers" to the TTS during its production. In general, these are liquid additives improving the absorption properties of human skin so that the active substance can be absorbed from a sufficiently small TTS-surface.

In particular readily volatile enhancers, e.g., ethanol frequently used for the active substance 17-β-estradiol, cause problems due to extreme softening of the patches' adhesive layers, therefore they require additional bulky compartments in the system, rendering the TTS unacceptably thick or voluminous. Finally, any additional non-polymeric additive involves the risk of intolerance phenomena on the skin, possibly even that of sensitization.

The addition of less volatile, however, mostly less active enhancers (e.g., glycerol esters, cyclic amides, eucalyptol) makes it possible to produce matrix systems comprising the active substance and absorption-promoting components in one or several monolithic layers. However, the adhesive strength of the patch remains unsatisfactory.

U.S. Pat. No. 4,863,738 represents one of many examples claiming the application of an active substance, e.g., 17-β-estradiol, together with an enhancer (in this case glycerol monooleate) in an optional concentration within a TTS-matrix.

According to the art, these TTSs do not permit a satisfactory therapy, either because the chosen enhancers have a poor skin tolerance, or the systems must have unacceptably large surfaces owing to insufficient active substance flow through the skin.

Dissolving more active substance molecularly disperse in the TTS than corresponds to the saturation solubility might be another possibility of increasing the active substance flow through the skin. With the degree of supersaturation of these systems the permeation rate through the skin is increased to the same extent. However, since supersaturated physical states are thermodynamically unstable, these forms of administration are not stable in storage. Spontaneous, unforeseeable precipitations of active substance particles will take place within months, or not later than years, so that the flow rate through the skin gradually decreases to the saturation flow level and a great deal of the initially existent therapeutic activity is lost.

The systems described in EP 0 421 454 comprise 17-β-estradiol in an acrylate polymer under addition of "crystallization inhibitors" and tackifying resins. Swelling agents are contained to give protection against premature loss of adhesive force.

A completely different way of avoiding thermodynamic instability is opened up in DE 42 37 453. It describes a transdermal therapeutic system having an active substance concentration ranging between the saturation solubility under moist conditions and that under dry conditions. A maximum ambient humidity of 10% is meant by "dry" conditions, and the achieved increase of skin permeation is stated to be about 50%.

SUMMARY OF THE INVENTION

It is the object of the present invention to provide a pharmaceutical preparation which, as compared to the prior art, results in higher active substances flows through the skin and does not undergo activity losses owing to recrystallization or active substance precipitation during storage.

According to the present invention this object is achieved in a pharmaceutical preparation according to the introductory part of claim 1 by the characterizing features stated in claim 1, by the fact that the estradiol amount contained in the preparation amounts to at least three times the saturation solubility amount measured at 95% atmospheric humidity, and that the air present in the package is adjusted to a relative air humidity of below 5%, preferably below 2% relative air humidity.

At room temperature and a relative air humidity between 20 and 60%, 17-β-estradiol is not present in an anhydric modification (I and II), but as a semihydrate (Busetti and Hospital, Acta Cryst. 1972, B28, 560). Owing to the layered structure stabilized via hydrogen bridges, and because of the diffusional compactness of the crystal compound, the hydrate can be subjected to a short-term heat treatment to temperatures of up to 170° C. without decomposition (Kuhnert-Brandstatter and Winkler (1976), Scientia Pharmaceutica 44 (3), 177–190).

With decreasing partial water vapor pressure, on the other hand, 17-β-estradiol has a higher solubility in some polymers, particularly in acrylate copolymers. This has already been known from DE 42 37 453; however, the extent of solubility increase to more than three times the amount has not been expected and is most surprising (Example 1), even in consideration of the art. According to Fick's law, higher active substance concentrations in a TTS with otherwise same conditions increase the diffusion flow through the skin; for this reason such a concentration increase in transdermal therapeutic systems is very advantageous. Thus, preparations manufactured according to the present invention can develop the same efficacy as prior-art systems, but with a smaller surface. However, absolute dry storage conditions are required to stabilize these properties.

These can preferably be ensured by gasproof and moistureproof packages, and by inserting moisture-absorbing products into the packing.

DETAILED DESCRIPTION OF THE INVENTION

The above-described invention may be realized in pharmaceutical preparations in different manners.

In an ointment, 17-β-estradiol is homogeneously distributed as an anhydrate or semihydrate according to usual methods by stirring under heating and adding to the ointment base an estradiol solution in a solvent, or by dispersing the micronized active substance. The simplest form of a percutaneous skin-adherent pharmaceutical preparation is a single-layer matrix system whose matrix, in addition to its function of delivering active substances, is pressure-sensitive adhesive at the same time, rendering an adhesive layer superfluous. However, the system may also be divided into several layers of the same or different composition and function.

If a membrane which is poorly permeable to estradiol is placed between such a matrix and a skin-facing adhesive layer, an active substance release is obtained which is controlled to a greater extent by the patch than by the skin. Such an active substance release may be advantageous if a very narrow margin of daily dosage is desired.

In this connection, acrylic acid copolymers are copolymers formed by radical polymerization of esters of acrylic acid and methacrylic acid with $C_1$- to $C_{18}$-alcohols, dimethylaminoethanol, or other suitable alcoholic reactants, vinyl acetate, vinylpyrrolidone, styrene, butadiene, acrylonitrile, or other suitable monomers with a vinyl group.

To render the system softer, 1,2-propanediol, 1,3-butylene glycol, 1-hexadecanol may be added, for example; or also 2-hydroxyfatty alcohols, 2-octyl dodecanol, 2-propanol, benzyl alcohol, cetylstearyl alcohol, diethylene glycol, dipropylene glycol, dodecanol, ethanol, glycerol, hexanediol, octanol, oleyl alcohol, panthenol, phenylethanol, polyethylene glycols, or polypropylene glycols; or fatty acids, such as, capric, linoleic, lauric, myristic acid, n-valeric acid, pelargonic acid; and also physiologically acceptable organic acids, such as, 3-phenylpropionic acid, acetic acid, adipic acid, benzoic acid, oleic acid, salicylic acid, or their salts well tolerated by the skin. Other compounds of this kind include—without claiming completeness—sulfates and sulfonates of fatty acids, esters of the formula $[CH_3(CH_2)_mCOO]R$, wherein m represents a number of 8 to 16, n 1 or 2, and R a short-chain alkyl chain; triglycerides, phthalates, sulfoxides, or amides.

The present invention will be illustrated in greater detail in the following with reference to Examples.

EXAMPLE 1

Production of a System According to the Present Invention 3.6 g 17-β-estradiol-semihydrate, micronized, and 150.4 g solution of an acrylate copolymer with a solids content of 37.5% are stirred at room temperature in a cylindrical glass vessel until a homogenous suspension results, subsequently this is coated on a siliconized polyester film having a thickness of 100 μm in such a manner that a layer thickness of 61 g/m² (relative to the solvent-free portion) results. This results in a portion of 6% (w/w) estradiol in the active substance-containing layer. The layer is dried for 10 minutes at 25° C. and for 15 minutes at 90° C., causing complete dissolution of the active substance under the influence of the heat. After that, a polyester film having a thickness of 15 μm is applied (laminated) as backing layer.

By punching using a steel rule cutting die, transdermal systems of 16 cm² are obtained which are stored
  a) at 31° C./70% relative humidity,
  b) at about 20–30° C. (room temperature), 0% relative humidity.

After 3 weeks of storage, the samples according to condition a) (prior art) show complete, macroscopically detectable crystallizations. In contrast to this, the samples of condition b) (according to the present invention) remain completely dissolved.

EXAMPLE 2

Production of a System (Comparative Example)

0.9 g 17-β-estradiol-semihydrate, micronized, and 157.6 g solution of an acrylate copolymer with a solids content of 37.5% are stirred at room temperature in a cylindrical glass vessel until a homogenous solution results, and are subsequently coated on a siliconized polyester film having a thickness of 100 μm in such a manner that a layer thickness of 58 g/m² (relative to the solventfree portion) results.

This results in a portion of 1.5% (w/w) freely dissolved estradiol in the active substance-containing layer.

The layer is dried for 10 minutes at 25° C. and for 15 minutes at 90° C.

After that, a polyester film having a thickness of 15 μm is applied (laminated) as backing layer.

By punching using a steel rule cutting die, transdermal systems of 16 cm² are obtained which are stored
  a) at 31° C./70% relative humidity,
  b) at about 20–30° C. (room temperature), 0% relative humidity.

After 3 weeks of storage, the samples according to condition a) show fine, microscopically easily detectable crystallizations.

The samples of condition b), however, remain completely dissolved.

The uniform supply of estradiol has proved to be effective for the prophylaxis of the Alzheimer's and Parkinson's disease (Scrip No.2026, p. 23; May 19, 1995). Therefore, this indication involves an ethically particularly significant application of the abovedescribed skin-adherent pharmaceutical preparations.

What is claimed is:

1. A pharmaceutical preparation for adhering to the skin, for the release of an active substance 17-β-estradiol, comprising 17-β-estradiol anhydrate dissolved in (meth)acrylate copolvmer by drying, the 17-β-estradiol being present in a concentration of at least three times the saturation solubility concentration measured at 95% relative air humidity, and wherein the pharmaceutical preparation is contained in a moisture-tight package having an amount of air enclosed within, wherein the enclosed air within the package is adjusted to a relative air humidity below 5%.

2. The preparation according to claim 1, wherein said preparation is a transdermal therapeutic system.

3. The preparation according to claim 1, wherein said preparation has a pressure-sensitive adhesive layer facing the skin and a non-tack backing layer averted from the skin.

4. The preparation according to claim 1, wherein said preparation comprises an acrylic-acid ester co-polymer.

5. The preparation according to claim 4 wherein the acrylic-acid ester copolymer at 0.1% relative air humidity comprises at least 6% (w/w) 17-β-estradiol in dissolved form.

6. The preparation according to claim 4 characterized in that the acrylic-acid ester copolymer at 0.1% relative air humidity comprises at least 8% (w/w) 17-β-estradiol in dissolved form.

7. A process for the production of primary packaged, skin-adherent pharmaceutical preparations according to claim 1, comprising preparing a solution or dispersion of 17-β-estradiol-semihydrate in a semisolid or liquid pharmaceutical base followed by coating it onto a film-like, anti-adhesive base material, drying the layer and applying a backing layer which is impermeable to active substances and moisture, and separating by blanking and film cutting, characterized in that drying is effected by immediate storage at an air humidity of below 5% relative humidity, up to complete dissolution of the contained estradiol, and by packing into gastight packages, optionally with addition of a moisture-absorbing material.

8. The process according to claim 7, wherein said drying is effected by immediate storage at an air humidity of below 2% relative humidity.

9. The process according to claim 7, wherein said drying is effected by immediate storage at an air humidity of below 0.5% relative humidity.

10. The preparation according to claim 1, wherein the air enclosed in the package is adjusted by the addition of a desiccant.

11. The preparation according to claim 10, wherein the air enclosed in the package is adjusted to a relative air humidity below 2%.

12. The preparation according to claim 10, wherein the air enclosed in the package is adjusted to a relative air humidity below 0.5%.

13. The preparation according to claim 1, wherein the pharmaceutical preparation additionally comprises an adhesive layer, and the adhesive layer contains 17 estradiol in dissolved form.

14. A method of treatment or prophylaxis of menopausal symptoms, osteoporosis or Alzeimer's disease, comprising:

applying the pharmaceutical preparation according to claim 1 to the skin of a subject.

* * * * *